(12) United States Patent
Worthen et al.

(10) Patent No.: US 7,507,823 B2
(45) Date of Patent: Mar. 24, 2009

(54) PROCESS OF MAKING ARIPIPRAZOLE PARTICLES

(75) Inventors: David R. Worthen, Lexington, KY (US); Simon Crawford Bristow, West Yorkshire (GB); Philip Michael Cocks, Huddersfield (GB)

(73) Assignee: Bristol-Myers Squibb Company, Princeton, NJ (US)

( * ) Notice: Subject to any disclaimer, the term of this patent is extended or adjusted under 35 U.S.C. 154(b) by 339 days.

(21) Appl. No.: 11/124,216

(22) Filed: May 6, 2005

(65) Prior Publication Data

US 2005/0272742 A1 Dec. 8, 2005

Related U.S. Application Data

(60) Provisional application No. 60/544,118, filed on May 6, 2004.

(51) Int. Cl.
C07D 241/04 (2006.01)
C07D 295/00 (2006.01)

(52) U.S. Cl. .................................................... 544/358

(58) Field of Classification Search ........................ None
See application file for complete search history.

(56) References Cited

U.S. PATENT DOCUMENTS

| | | | |
|---|---|---|---|
| 4,404,183 A | 9/1983 | Kawata et al. |
| 4,734,416 A | 3/1988 | Banno et al. |
| 4,914,094 A | 4/1990 | Oshiro et al. |
| 5,006,528 A | 4/1991 | Oshiro et al. |
| 5,314,506 A | 5/1994 | Midler, Jr. et al. |
| 5,424,076 A | 6/1995 | Gorissen et al. |
| 5,466,823 A | 11/1995 | Talley et al. |
| 5,474,995 A | 12/1995 | Ducharme et al. |
| 5,563,165 A | 10/1996 | Talley et al. |
| 5,622,978 A | 4/1997 | Ciceri et al. |
| 5,807,873 A | 9/1998 | Nicolai et al. |
| 6,108,651 A | 8/2000 | Guha |
| 6,302,958 B1 | 10/2001 | Lindrud et al. |
| 2003/0129753 A1 | 7/2003 | Lee |
| 2004/0058935 A1 | 3/2004 | Bando et al. |

FOREIGN PATENT DOCUMENTS

| | | |
|---|---|---|
| EP | 0 367 141 | 1/1996 |
| EP | 0 852 140 | 12/2003 |
| EP | 1 475 084 | 11/2004 |
| GB | 2 355 194 | 4/2001 |
| GB | 2 381 453 | 5/2003 |
| WO | WO 95/01221 | 1/1995 |
| WO | WO 96/31202 | 10/1996 |
| WO | WO 97/31691 | 9/1997 |
| WO | WO 97/39050 | 10/1997 |
| WO | WO 98/13136 | 4/1998 |
| WO | WO 99/15503 | 4/1999 |
| WO | WO 99/25322 | 5/1999 |
| WO | WO 00/56726 | 9/2000 |
| WO | WO 01/03821 | 1/2001 |
| WO | WO 01/15664 | 3/2001 |
| WO | WO 01/41765 | 6/2001 |
| WO | WO 01/47492 | 7/2001 |
| WO | WO 01/85135 | 11/2001 |
| WO | WO 02/38127 | 5/2002 |
| WO | WO 03/026659 | 4/2003 |
| WO | WO 2004/060347 | 7/2004 |
| WO | WO 2004/063162 | 7/2004 |
| WO | WO 2004/078161 | 9/2004 |
| WO | WO 2004/078163 | 9/2004 |
| WO | WO 2004/106322 | 12/2004 |
| WO | WO 2005/000811 | 1/2005 |
| WO | WO 2005/041970 | * 5/2005 |

OTHER PUBLICATIONS

Reid et al. The Porperties of Gases and Liquids, 1977, p. 142.*
U.S. Appl. No. 10/701,229, filed Nov. 4, 2003, Harland et al.
Chiou, W.L. et al., "Pharmaceutical Applications of Solid Dispersion Systems", Journal of Pharmaceutical Sciences, vol. 60, No. 9, pp. 1281-1302 (1971).
de Villiers, M.M. et al., "X-Ray powder diffraction determination of the relative amount of crystalline acetaminophen in solid dispersions with polyvinylpyrrolidone", International Journal of Pharmaceutics, vol. 163, pp. 219-224 (1998).
Debenedetti, P.G. et al., "Application of supercritical fluids for the production of sustained delivery devices", Journal of Controlled Release, vol. 24, pp. 27-44 (1993).
Ford, J.L., "The Current Status of Solid Dispersions", Pharm. Acta Helv., vol. 61, No. 3, pp. 69-88 (1986).
Gennaro, A.R., ed., Remington: The Science and Practice of Pharmacy, 20th Edition, Lippincott Williams & Wilkins, publ., pp. xiv-xv (2000) (table of contents).
Goldberg, A.H. et al., "Increasing Dissolution Rates and Gastrointestinal Absorption of Drugs Via Solid Solutions and Eutectic Mixtures II", Journal of Pharmaceutical Sciences, vol. 55, No. 5, pp. 482-487 (1966).
Goldberg, A.H. et al., "Increasing Dissolution Rates and Gastrointestinal Absorption of Drugs Via Solid Solutions and Eutectic Mixtures III", Journal of Pharmaceutical Sciences, vol. 55, No. 5, pp. 487-492 (1966).
Jung, J.-Y. et al., "Enhanced solubility and dissolution rate of itraconazole by a solid dispersion technique", International Journal of Pharmaceutics, vol. 187, pp. 209-218 (1999).

(Continued)

*Primary Examiner*—James O. Wilson
*Assistant Examiner*—Noble Jarrell
(74) *Attorney, Agent, or Firm*—Burton Rodney

(57) ABSTRACT

A method of preparation of crystalline aripiprazole monohydrate includes the use of solution enhanced dispersion by supercritical fluid. Specifically, water is introduced to a stream of supercritical fluid which is then allowed to mix with a stream including a mixture including aripiprazole and a solvent. The mixing results in the substantially simultaneous dispersion and extraction of the aripiprazole from the mixture by the supercritical fluid.

18 Claims, 2 Drawing Sheets

OTHER PUBLICATIONS

Kapsi, S.G. et al., "Processing factors in development of solid solution formulation of itraconazole for enhancement of drug dissolution and bioavailability", International Journal of Pharmaceutics, vol. 229, pp. 193-203 (2001).

Rasenack, N. et al., "Dissolution Rate Enhancement by *in Situ* Micronization of Poorly Water-Soluble Drugs", Pharmaceutical Research, vol. 19, No. 12, pp. 1894-1900 (2002).

Sekiguchi, K. et al., "Studies on Absorption of Eutectic Mixture. I. A Comparison of the Behavior of Eutectic Mixture of Sulfathiazole and that of Ordinary Sulfathiazole in Man", Chemical & Pharmaceutical Bulletin, vol. 9, pp. 866-872 (1961).

Serajuddin, A.T.M., "Solid Dispersion of Poorly Water-Soluble Drugs: Early Promises, Subsequent Problems, and Recent Breakthroughs", Journal of Pharmaceutical Sciences, vol. 88, No. 10, pp. 1058-1066 (1999).

Takeuchi, H. et al., "Spherical Solid Dispersion Containing Amorphous Tolbutamide Embedded in Enteric Coating Polymers or Colloidal Silica Prepared by Spray-Drying Technique", Chem. Pharm. Bull., vol. 35, No. 9, pp. 3800-3806 (1987).

Taylor, L.S. et al., "Spectroscopic Characterization of Interactions Between PVP and Indomethacin in Amorphous Molecular Dispersions", Pharmaceutical Research, vol. 14, No. 12, pp. 1691-1698 (1997).

* cited by examiner

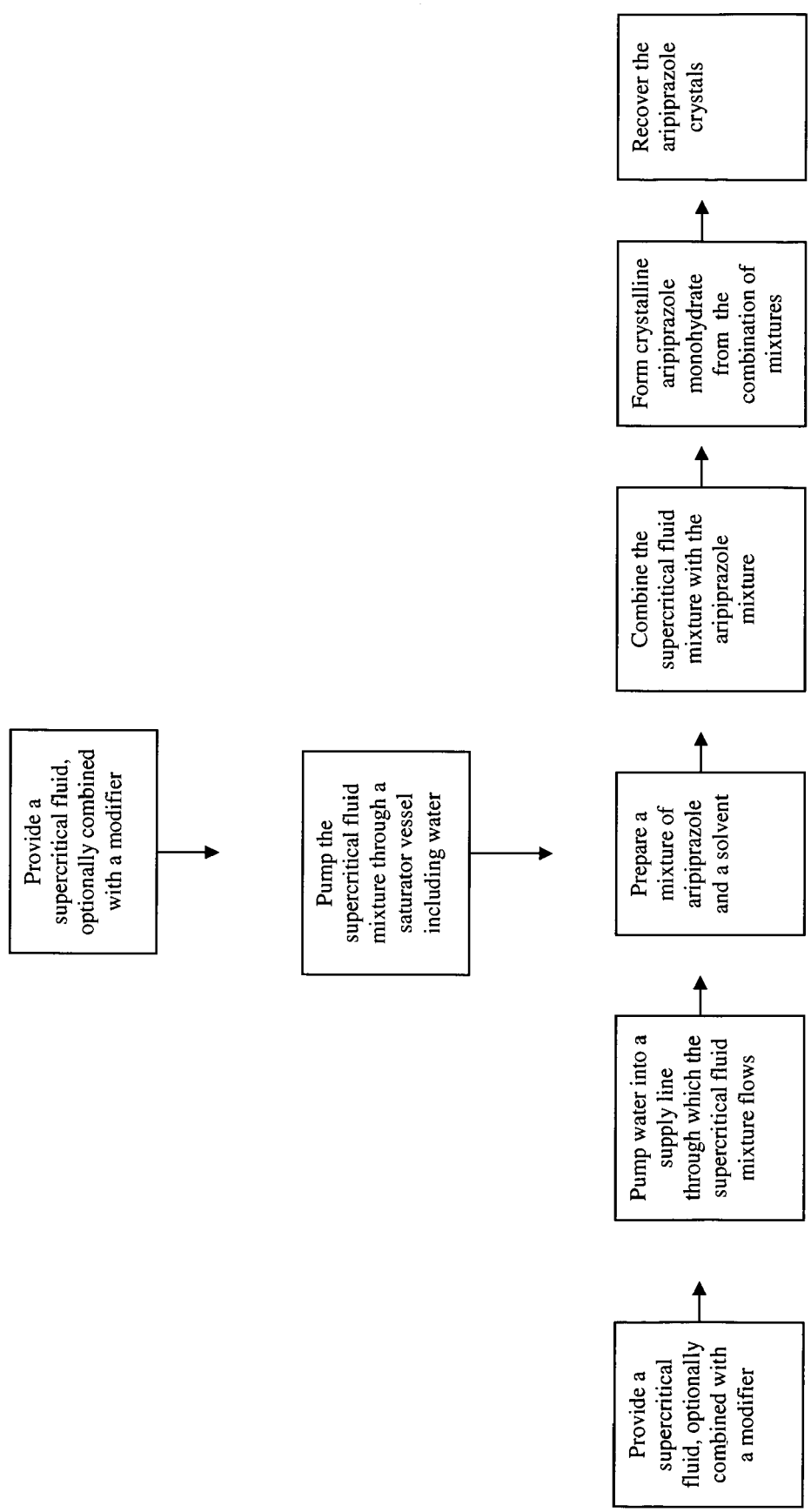

PROCESS OF MAKING ARIPIPRAZOLE PARTICLES

This application claims priority from U.S. Provisional Application No. 60/544,118, filed May 6, 2004, incorporated in its entirety herein by reference.

FIELD OF THE INVENTION

The present invention relates to a process for the preparation of aripiprazole particles, specifically crystalline aripiprazole monohydrate. The process includes technology related to solution enhanced dispersion by supercritical fluid.

BACKGROUND OF THE RELATED TECHNOLOGY

Aripiprazole, 7-(4-[4-(2,3-dichloropheny)-1-piperazinyl]-butoxy)-3,4-dihydro carbostyril or 7-(4-[4-(2,3-dichloropheny)-1-piperazinyl]-butoxy)-3,4-dihydro-2(1H)-quinolone, is a drug useful as an antipsychotic treatment, as described in U.S. Pat. Nos. 4,737,416 and 5,006,528. The structure of aripiprazole is shown below.

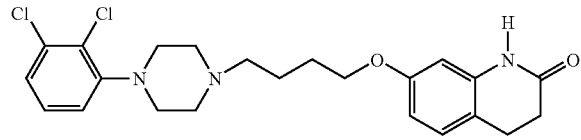

Several polymorphic forms of aripiprazole have been identified. These include six anhydrous polymorphic forms, designated types I to VI, two pseudo polymorphs, a monohydrate and a ½ ethanolate. These polymorphic forms have been disclosed, for example, in Patent Publication Nos. US2004058935 and WO 03/026659. Aripiprazole anhydrate may be used for the formulation of therapeutic treatments, however the hygroscopic nature of these crystals has made them difficult to handle, particularly to prevent exposure to moisture. Upon exposure to water, the anhydrous forms take up water and are converted to a hydrous form or hydrate. The hydrates are however less bioavailable and result in a slower dissolution rate than the anhydrous forms. Recently, WO 03/026659 disclosed various polymorphic forms of aripiprazole anhydrate, including an Anhydrate B form having reduced ygroscopicity, and which was thus more amenable to pharmaceutical processing and formulation. This Anhydrate is prepared via a process in which a hydrous form, Hydrate A, serves as an intermediate. This hydrate is prepared from the milling of what is known as Conventional Hydrate, as is disclosed in WO 03/026659. The Hydrate A is then transformed to Anhydrate B through a heating process.

The Hydrate A, also known herein as aripiprazole monohydrate, though demonstrating usefulness as an intermediate, has a low solubility in water and thus also presents certain processing challenges. The known process of preparing it from Conventional Hydrate by milling has obvious drawbacks in reduced processing efficiency and cost. It is therefore desirable to identify a method of preparing aripiprazole monohydrate suitable for use in the preparation of the anhydrate forms.

Generally, the preparation of particles of pharmaceutical compounds of low aqueous solubility has been addressed, for example, by co-formulation with polymers or other excipients that act as carriers, fillers and/or modifiers. In such modes of preparation, the pharmaceutical compound and the polymer or excipient are co-precipitated from a solvent system in which both are dissolved. Alternatively, the particles may be formed using a solution enhanced dispersions (SEDS) system, in which fine particles of a poorly soluble material are coated with a solubility-enhancing material, first starting with a suspension of particles of the pharmaceutical compound in a solution of the coating material. Such a process is taught in Published PCT Application No. WO 96/00610. Using this method, however, the particles must be prepared beforehand and coated in a separate step.

A method for the preparation of particles of poorly soluble materials using supercritical fluids is disclosed in U.S. Pat. No. 5,851,453 to Hanna et al. ("Hanna"). Hanna describes an apparatus and method for preparing particles by solution enhanced dispersion by supercritical fluid (SEDS). According to Hanna's method, SEDS processing includes controlling the temperature and pressure of a particle formation vessel into which a supercritical fluid and a mixture including a substance that is either in solution or suspension are co-introduced. The combination of the supercritical fluid and the substance-containing mixture results in the substantially simultaneous dispersion and extraction of the substance from the mixture by the supercritical fluid.

While Hanna gives examples of solids that may be used with the process, there is no disclosure of what properties a solid must possess to be prepared with the process. Furthermore, Hanna does not describe a process for the preparation of a crystalline aripiprazole monohydrate.

U.S. Pat. No. 6,461,642 to Bisrat et al. ("Bisrat") also describes a preparation for particles using a SEDS technique. However, this process is directed toward the preparation of powders for pulmonary administration.

In view of the foregoing discussion and recognition of the problems associated with preparation of pharmaceutical compounds in general, and aripiprazole anhydrates in particular, it would seem desirable to provide a process for the preparation of crystalline aripiprazole monohydrate from unprocessed aripiprazole that provides particles of a size useful for the preparation of an anhydrate form, or for incorporation into pharmaceutical formulations, for example suspensions for intramuscular administration.

SUMMARY OF THE INVENTION

The present invention provides a process for the preparation of crystalline aripiprazole monohydrate from unprocessed aripiprazole comprising providing a first mixture comprising a solvent and unprocessed aripiprazole, providing a second mixture comprising a supercritical fluid and optionally, a modifier, introducing water to the second mixture, introducing the first mixture to the second mixture in a particle formation vessel, wherein the contacting of the first mixture with the second mixture produces crystalline aripiprazole monohydrate, and recovering the crystalline aripiprazole monohydrate. Compared to the conventional process of milling used to prepare Hydrate A, as described in the art, this process utilizes a solution enhanced dispersion system (SEDS) technology.

As used herein, the term "unprocessed aripiprazole" is meant to include any of the polymorphic forms of aripiprazole, including any crystalline forms, whether anhydrates or conventional hydrate, or aripiprazole in the amorphous state, any of which may be present in combination in the starting material. The term "conventional hydrate" means a hydrated form of aripiprazole formed either during synthesis or by hygroscopic conversion of an anhydrate form, which has not been further processed to yield the monohydrate also known as Hydrate A. The term "contacting," as used in reference to the process of mixing a first mixture with a second mixture, means combining the two mixtures to facilitate contact of the finely divided unprocessed aripiprazole with a supercritical fluid to promote molecular rearrangement and the formation of crystals.

In another embodiment, the invention comprises a process for preparing a crystalline aripiprazole monohydrate from unprocessed aripiprazole comprising the steps of providing a first mixture comprising n-propanol and unprocessed aripiprazole, providing a second mixture comprising supercritical carbon dioxide and optionally, a modifier. Preferably, the process includes introducing water to the second mixture at a flow rate of about 0.2 L/min or less, introducing the first mixture, at a flow rate of about 0.4 mL.min$^{-1}$ or less, and the second mixture at a flow rate of about 0.9 mL/min or greater, into a particle formation vessel to produce crystalline aripiprazole monohydrate, and recovering the crystalline aripiprazole monohydrate.

The processes according to these representative embodiments of the invention incorporate a SEDS technique. Generally, the process of preparing the crystalline aripiprazole monohydrate includes combining a mixture of a solvent and the unprocessed aripiprazole and a second mixture including a supercritical fluid and optionally a modifier. Water is then introduced to the second mixture to saturate or partially saturate the supercritical fluid, which in certain embodiments may be carbon dioxide. The first and second mixtures are then contacted in a particle formation chamber to produce the crystalline aripiprazole monohydrate. Desirably, the introduction of the first and second mixtures into the particle formation chamber occurs simultaneously. Upon contact between the two mixtures, the crystalline aripiprazole monohydrate is formed and agglomerated into particles which may then be recovered.

A further aspect of the present invention provides a crystalline aripiprazole monohydrate having a particle size range from about 1 μm to about 75 μm, preferably from about 2 μm to about 25 μm, most preferably from about 2 μm to about 10 μm That is produced by a process that includes the steps of first providing a mixture of a solvent and the unprocessed aripiprazole and providing a second mixture including a supercritical fluid and optionally a modifier. Water is then introduced to the second mixture to saturate or partially saturate the supercritical fluid, which may be carbon dioxide. The first and second mixtures are then introduced to a particle formation chamber to produce the crystalline aripiprazole monohydrate. Finally, the crystalline aripiprazole monohydrate particles are recovered.

BRIEF DESCRIPTION OF THE DRAWINGS

FIG. 2 is a flow diagram describing an alternate schematic process for preparing crystalline aripiprazole monohydrate.

DETAILED DESCRIPTION OF THE INVENTION

Figure 1:
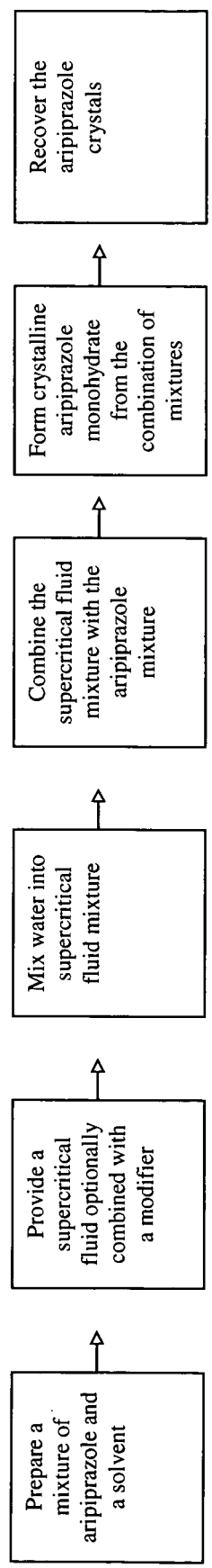
FIG. 1 is a flow diagram describing a schematic process for preparing crystalline aripiprazole monohydrate.

The unprocessed aripiprazole for use as a starting material in the present invention may be selected from conventional hydrate, anhydrates, amorphous forms and combinations thereof.

An aripiprazole material suitable for use as an unprocessed aripiprazole in the invention may be prepared according to the process described in U.S. Pat. Nos. 5,006,528, 4,734,416 and 4,914,094 and related applications, the entire disclosures of which are herein incorporated by reference. For example, aripiprazole can be prepared by the reaction of a carbostyril compound with a piperazine compound according to the following general scheme:

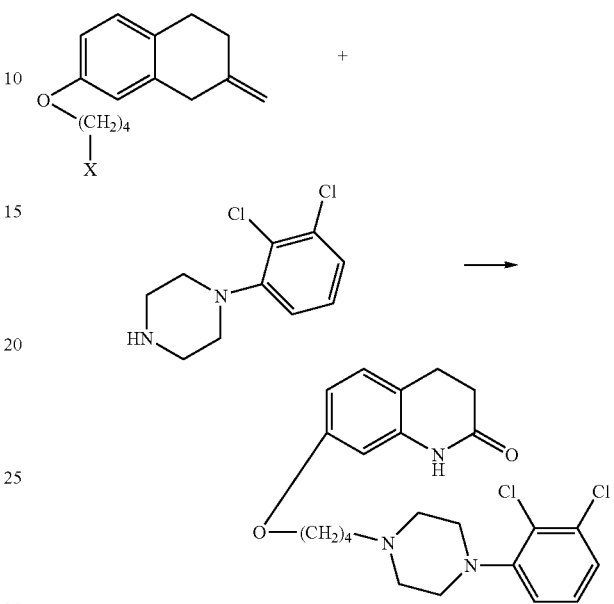

where X is halogen, a lower alkanesulfonyloxy group, an arylsulfonyloxy group, an aralkylsulfonyloxy group, in the presence of an inorganic or organic basic compound, in an organic solvent or in the absence of solvent. Such a reaction is described, for example, in published European Patent EP 367141B1, the related disclosure of which is herein incorporated by reference. An improved process for the preparation of aripiprazole has also been developed that includes reacting a carbostyril compound with a piperazine compound and/or salt thereof in water, in the presence of an inorganic basic compound present in an amount of from 0.5 to 10 mol per mol of the carbostyril compound. Such a process is described in published Patent Application WO 2004/063162, the related disclosure of which is also herein incorporated by reference. The product of the synthesis is typically an oily substance which may be isolated, extracted, purified and/or crystallized to provide dry, solid product.

As otherwise mentioned herein, in various embodiments the starting material may be an aripiprazole hydrate that includes the material referred to herein as a conventional hydrate. This hydrate may be distinguished from the monohydrate formed according to the practice of this invention. Since the latter reaction described above uses water, at least a portion of the product may include such a hydrous form. Moreover, because of the hygroscopicity of the material produced by either method, conversion to a hydrous form may be anticipated.

The hydrate starting material can be milled via conventional milling methods to form a monohydrate characterized, in part, by a grain size of about 50 μm or less, preferably about 30 μm or less. Grain size may be determined according to the following procedure: 0.1 g of the grains to be measured were suspended in a 20-ml n-hexane solution of 0.5 g soy lecithin, and grain size was measured using a size distribution meter (Microtrack HRA, Microtrack Co.)

Crystalline aripiprazole monohydrate (Hydrate A) can be characterized by certain ordinarily determined physicochemical characteristics:

(1) It has an endothermic curve thermogravimetric/differential thermal analysis (heating rate 5° C./min) characterized by the appearance of a small peak at about 71° C. and a gradual endothermic peak around 60° C. to 120° C.

(2) It has an $^1$H-NMR spectrum which has characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

(3) It has a powder x-ray diffraction spectrum which has characteristic peaks at 2θ=12.6°, 15.4°, 17.3°, 18.0°, 18.6°, 22.5° and 24.8°.

(4) It has clear infrared absorption bands at 2951, 2822, 1692, 1577, 1447, 1378, 1187, 963 and 784 cm$^{-1}$ on the IR (KBr) spectrum.

(5) It has a mean grain size of 50 μm or less.

The previously known process for preparing aripiprazole monohydrate requires milling of the conventional hydrate, as described above. In preparing the monohydrate according to the process of the invention, a first mixture is prepared which includes the unprocessed aripiprazole and at least one organic solvent. Ideally, the aripiprazole dissolves in the solvent forming a solution. The solvent may be any suitable solvent known in the art. Non-limiting examples of suitable solvents for the first mixture include methanol, ethanol, n-propanol (n-PrOH), isopropanol, n-butanol, iso-butanol, sec-butanol, ethyl acetate, acetonitrile, tert-butanol, an aldehyde, acetone, dimethylsulfoxide, tetrahydrofuran (THF), dichloromethane, dimethyl formamide (DMF), and combinations thereof.

The first mixture may also include water. The water may either be added directly to the first mixture, introduced into a supply line through which the first mixture flows, or added as the first and second mixtures are combined, which may be through the use of a coaxial nozzle or through a separate stream that will mix with the streams of the first and second mixtures at the particle formation vessel.

A second mixture is also prepared which includes a supercritical fluid and optionally a modifier. The modifier may be present in an amount from about 0 to about 20% by weight, desirably from about 1% to about 20% of the second mixture. The modifier may also be referred to as a co-solvent. In general, a modifier is added to change the intrinsic properties of the supercritical fluid in or around the critical point. In the present invention, the modifier serves the purpose of aiding the removal of water. It is important that the modifier or co-solvent be either completely miscible with, or be at least partially soluble in both the supercritical fluid and water. Considering that water is almost insoluble in supercritical carbon dioxide, the presence of the modifier allows excess water to be removed from the system.

A variety of supercritical fluids may be used with the present invention. These include carbon dioxide, nitrous oxide, sulfur hexafluoride, xenon, ethylene chlorotrifluoromethane, ethane, trifluoromethane, and combinations thereof. Desirably, the supercritical fluid includes carbon dioxide.

A variety of solvents may also be used as the modifier or co-solvent. Non-limiting examples include methanol, ethanol, n-propanol (n-PrOH), isopropanol, n-butanol, iso-butanol, sec-butanol, tert-butanol, an aldehyde, acetone, dimethylsulfoxide, tetrahydrofuran (THF), dichloromethane, dimethyl formamide (DMF), and combinations thereof.

Prior to the combination of the first and second mixtures, water is introduced to the second mixture. This may be accomplished by a variety of methods. These include pumping the water into a supply line through which the second mixture flows, or pumping the second mixture through a saturator vessel comprising water.

Where the water is introduced to the supercritical fluid by feeding it into the supply line, this is typically accomplished at a low flow rate, for example about 0.4 mL/min or less. Desirably, this occurs prior to the second mixture passing through heat exchanger coils. This allows the supercritical fluid and the water to mix fully and homogenize at the elevated temperature before contacting the first mixture. Also, prior to contact with the first mixture, excess water may collect in a pulse damper vessel, upstream of the particle formation vessel. This serves to minimize the carry over of water into the final aripiprazole product.

When a saturator vessel is used to introduce the water to the second mixture, the saturator vessel is connected in-line to the supercritical fluid supply line. The vessel may be approximately a 500 mL vessel including up to about 100 mL of purified water. The vessel may also be packed with small stainless steel coils to increase the surface area and aid equilibration by enhancing the contact area between the water and the super critical fluid. The supercritical fluid passes through the vessel to incorporate a small proportion of water at its saturation level, i.e., about 1% or less.

The first and second mixtures flow through separate channels prior to mixing. The mixing occurs at the particle formation vessel. Desirably, the mixtures are introduced to the particle formation vessel simultaneously. At the particle formation vessel, the first and second mixtures are combined by the use of a specifically designed nozzle. This may be a sonic nozzle, with an aperture of approximately 0.2 mm. With the sonic nozzle, the second mixture exits the nozzle, into the particle formation vessel as it meets the first mixture which enters the vessel through a separate channel. The streams of the first and second mixtures meet close to the nozzle opening, i.e., approximately 4 mm from the nozzle opening.

A coaxial nozzle, with the outlet end in communication with the particle formation vessel, may also be used. This nozzle will have two or more passages which terminate adjacent to one another at the outlet end. At least one passage will carry the flow of the supercritical fluid mixture and at least one passage will carry the mixture including the aripiprazole mixture. Typically, the outlet end of the nozzle will have a diameter of approximately 0.2 mm. However, a suitable range is from about 0.05 mm to about 2 mm, desirably from about 0.1 mm to about 0.3 mm.

After the desired production of aripiprazole, the introduction of water and the first mixture (containing the aripiprazole) are discontinued. Then additional amounts of the second mixture, including the supercritical fluid, are allowed to flow through the particle formation vessel. Alternatively, the supercritical fluid alone may be allowed to flow through the vessel. This promotes the removal of excess water that may be present in the vessel after particle formation.

The process operating parameters for the present invention, including the pressure, temperature, solution concentration and flow rates may be manipulated to control the size, shape and morphology of the monohydrate crystals. With regard to the flow rate, the first mixture will have a flow rate of about 0.4 mL/min or less and the second mixture will have a flow rate of about 9 mL/min or greater. Desirably, the particle size of the crystalline aripiprazole monohydrate will be from about 2 µm to about 25 µm, more desirably from about 2 µm to about 10 µm.

The features and advantages of the present invention are more fully shown by the following examples which are provided for purposes of illustration, and are not to be construed as limiting the invention in any way.

EXAMPLES

Several trial runs were performed using various parameters as shown in Tables 1-4. Analysis of each of the samples was performed by Differential Scanning Calorimetry (DSC) and X-Ray Powder Diffraction (XRPD).

Thermal analyses were carried out under PERKIN ELMER® SERIES 7 Thermal Analysis Apparatus (Perkin-Elmer, USA). DSC was used extensively to determine the particular polymorphic form by observing the presence or absence of a dehydration peak at about 100° C.

DSC revealed changes during the heating of a sample, which involved evolution or adsorption of energy. A sample (2-10 mg) and a chemically inert reference material were placed in sealed, crimped aluminum pans and slowly heated in separate cells under a nitrogen atmosphere. When a difference in temperature between the two sample cells was detected, due to a physical or chemical transition in the test substance, the cooler of the two samples was heated until the difference was eliminated. The electrical energy needed to accomplish this was then plotted against temperature. An endothermic change indicated that an enthalpy increase had occurred, and exothermic change indicated that an enthalpy decrease had occurred. The transition position and shape of the peak give information on the temperature range in which a transition took place and the type of phase change that had occurred, respectively. Peak analysis was carried out using the Perkin-Elmer thermal analysis software which controlled all thermal analysis techniques.

For analysis of the trial products, a heating rate of 10° C./min over the range of 20° C. to 160° C. was generally employed.

X-ray powder diffraction (XRPD) was carried out using a Siemens model D-5000 diffractometer (Karlsruhe, Germany). Many materials are crystalline and thus show some external and internal symmetry and regularity. This symmetry (termed crystal structure) can be made visible by XRPD. When a material is irradiated by monochromatic X-rays, a pattern is obtained which is characteristic (a fingerprint) of that material. Hence specific compounds may be identified.

Test samples of unprocessed aripiprazole were prepared by placing them in a mortar and pestle and grinding to a fine powder. This produced thousands of small crystallites and ensured sample homogeneity. Each test sample was placed in a standard sample holder and inserted into the diffractometer. Data were collected between 2° and 40° in a stepwise mode (increasing 0.05° at a count interval of three seconds). Calculations of d-spacings and intensity values were made using the integrated instrument software on an adjacent PC, and compared to literature values for sample identification.

Comparative Examples (Runs 1-21)

Organic Solvent/Water Combinations

Small volumes of water were added directly into the drug solution, i.e. the first mixture, to maintain a single solution while providing sufficient water vapor within the system to promote hydrate formation. The process parameters and results for the runs that included water with the aripiprazole mixture are shown in Table 1 and Table 2. Various trials were carried out using acetone, DMF, THF and n-propanol as the organic solvent component, with the primary aim of producing the monohydrate polymorph. These solvents were all completely miscible with water and capable of removing any excess, unassociated water from the system prior to extraction by supercritical carbon dioxide. The level of aripiprazole solubility was found to differ significantly in these solvents, so the effect of the solute-solvent interactions could also be observed. Generally high $CO_2$ flows>9 ml $min^{-1}$ were employed in combination with low solution flows<0.4 ml $min^{-1}$, to produce rapid supersaturation and a high degree of dispersive energy. Various temperatures and pressures were utilized. The effect of adding up to 10% v/v water directly into acetone solutions, 5% v/v water in DMF solutions and as high as 25% v/v in THF solutions was investigated. Free flowing, crystalline, white powders were consistently produced in high yields (>75% w/w).

The material produced from the experiments shown in Tables 1 and 2 was anhydrous, as determined by the absence of a dehydration peak on the DSC trace and by XRPD, which gave the characteristic anhydrous form N1 diffractogram. An example of uniform crystalline particles <10 µm in size (81% yield), was obtained from run 11. The particles produced possessed a flat platelet habit when observed under SEM (scanning electron microscopy). The characteristic anhydrous polymorph was confirmed by XRPD.

As noted in runs 17-19 and 21, n-propanol (n-PrOH) had the effect of significantly reducing pressure fluctuations at the nozzle. The solubility of aripiprazole in n-PrOH is low, only about 7 mg/ml. Therefore, a highly saturated solution could be produced with a very low solution concentration. At such low concentrations, the number of nucleation sites within the nozzle is low enough to prevent substantial blockages. When processing n-PrOH solutions at 4% to 6.5% w/v, pressure fluctuations were reduced to a more satisfactory level of <35 bar. The use of n-PrOH also had a direct effect on particle morphology and size. Water was again incorporated into the solution, in an attempt to produce the monohydrate. At 150 bar and 70° C., processing a 91:9 v/v n-PrOH:$H_2O$ solution at 4 mg/ml, resulted in the formation of small, uniform particles of low aspect ration (Table 1-run 18). The flat, well faceted, 4-6 sided crystals had a narrow size distribution and volume median diameter (VMD) of 4.5 µm. The sample was, however, anhydrous. An additional experiment showed that anhydrous material was still produced from an n-PrOH solution containing 15% v/v water. The DSC trace of this material (Table 2-run 19) also showed only a single melt peak at 138.9° C.

These preliminary SEDS experiments, the comparative example of runs 1-21, the results of which are shown in Tables 1-2, highlighted the difficulty of obtaining the monohydrate when using the straightforward approach of adding small volumes of water directly into the organic/drug solution. Without wishing to be limited to one theory, a possible explanation for this is that the solvent/water and the solvent/water/$CO_2$ interactions are simply stronger than the solute-water interaction. Therefore, free water vapor is not made available within the system, because the organic solvent interacts with the water molecules, which are then extracted directly into the carbon dioxide along with the modifier. Water cannot associate itself with the weakly interacting solute molecules and as a result anhydrous crystalline material is formed.

TABLE 1

ORGANIC SOLVENT/WATER MIXTURE

| Run | Solvent (v/v) | Soln conc. (w/v) | Soln flow (ml/min) | CO Flow (ml/min) | Pressure (bar) | Temp (° C.) | ΔP (bar) | Nozzle (mm) | Yield (%) | VMD (μm) |
|---|---|---|---|---|---|---|---|---|---|---|
| 1 | Acetone:H$_2$O (95:5) | 1.0 | 0.2 | 9 | 150 | 50 | 100 | 0.2 | 86 | — |
| 2 | Acetone:H$_2$O (95:5) | 1.0 | 0.2 | 9 | 150 | 50 | >170 | 0.2 | 73 | — |
| 3 | Acetone:H$_2$O (95:5) | 1.0 | 0.2 | 20 | 150 | 50 | >170 | 0.2 | 56 | — |
| 4 | Acetone:H$_2$O (95:5) | 0.7 | 0.4 | 20 | 150 | 50 | >150 | 0.2 | 89 | 6.2 |
| 5 | DMF:H$_2$O (95:5) | 3.0 | 0.2 | 9 | 200 | 70 | 60 | 0.2 | 93 | 9.4 |
| 6 | DMF:H$_2$O (95:5) | 3.0 | 0.2 | 10 | 200 | 40 | >150 | 0.2 | 74 | — |
| 7 | DMF:H$_2$O (95:5) | 3.0 | 0.2 | 18 | 150 | 50 | 2 | None | 83 | — |
| 8 | Acetone:H$_2$O (95:5) | 0.7 | 0.2 | 20 | 150 | 50 | 5 | None | 85 | — |
| 9 | DMF:H$_2$O (95:5) | 9.0 | 0.2 | 20 | 200 | 80 | >150 | 0.75 | 65 | — |
| 10 | DMF:H$_2$O (95:5) | 7.0 | 0.2 | 20 | 90 | 80 | 50 | 0.75 | 75 | — |
| 11 | THF:H$_2$O (95:5) | 3.0 | 0.2 | 20 | 200 | 40 | 120 | 0.2 | 81 | 5.5 |
| 12 | THF:H$_2$O (95:5) | 10.0 | 0.2 | 20 | 200 | 40 | OP | None | — | — |
| 13 | THF:H$_2$O (95:5) | 3.0 | 0.2 | 20 | 200 | 40 | >150 | 0.3 | — | — |
| 14 | THF:H$_2$O (95:5) | 3.0 | 0.2 | 20 | 200 | 40 | OP | 0.2 | 85 | — |
| 15 | THF:H$_2$O (95:5) | 1.0 | 0.4 | 20 | 200 | 40 | >150 | 0.2 | 83 | 9.2 |
| 16 | Acetone:H$_2$O (90:10) | 0.5 | 0.2 | 9 | 150 | 60 | 100 | 0.1 | 83 | — |
| 17 | n-PrOH:H$_2$O (94:6) | 0.4 | 0.3 | 18 | 150 | 80 | 8 | 0.2 | 78 | 6.3 |
| 18 | n-PrOH:H$_2$O (91:9) | 0.4 | 0.3 | 20 | 150 | 70 | 5 | 0.2 | 57 | 4.5 |
| 19 | n-PrOH:H$_2$O (85:15) | 0.4 | 0.3 | 20 | 150 | 70 | 15 | 0.2 | 81 | 8.5 |
| 20 | THF:H$_2$O (75:25) | 1.0 | 0.2 | 20 | 200 | 60 | 60 | 0.2 | 81 | 11.0 |
| 21 | n-PrOH:H$_2$O (90:10) | 0.4 | 0.3 | 12 | 150 | 70 | 40 | 0.2 | 85 | — |

VMD = volume median diameter
ΔP = change in pressure at nozzle aperture

TABLE 2

ORGANIC SOLVENT-WATER MIXTURE

| Run | Morphology (SEM) | DSC/XRPD | Notes |
|---|---|---|---|
| 1 | Non-uniform plates | N1/monohydrate mixture | — |
| 2 | Non-uniform plates | N1/monohydrate mixtures | — |
| 3 | Small plates 2-10 μm | anhydrous/N1 | Increasing CO$_2$ flow yields anhydrous polymorph |
| 4 | Small plates 2-10 μm | Anhydrous/N1 | Increasing CO$_2$ flow yields anhydrous polymorph |
| 5 | Non-uniform plates | — | — |
| 6 | Small plates 5-20 μm | — | Increased pressure build up |
| 7 | Irregular plates/bars | — | Flow through nozzle to remove any fluctuations in pressure |
| 8 | Irregular plates/bars | — | Flow through nozzle to remove any fluctuations in pressure |
| 9 | — | — | Run abandoned. Solution crashing out |
| 10 | — | — | Lumpy product-crystalline acicular particles produced. |
| 11 | Small, very uniform plates 2-8 μm | Anhydrous/N1 | Very static powder (Large ΔP) |
| 12 | — | — | Flow through nozzle. Solution crashing out. |

TABLE 2-continued

ORGANIC SOLVENT-WATER MIXTURE

| Run | Morphology (SEM) | DSC/XRPD | Notes |
|---|---|---|---|
| 13 | — | — | Repeat of 11 with increased nozzle aperture (Still Large ΔP) |
| 14 | — | — | Direct repeat of 11. Pumps overpressured |
| 15 | Small, aggregate plates 5-10 μm | — | Increased water content |
| 16 | Non-uniform plates | Possible hydrate - undetermined | Poor particles |
| 17 | Small, uniform plates <10 μm | anhydrous | Narrow size distribution. Small ΔP |
| 18 | Small, hexagonal plates, 3-8 μm in size | anhydrous | Tiny ΔP. Very narrow size distribution (smallest particles) |
| 19 | Irregular particles, rounded and plates | anhydrous | Anhydrous at 15% water. Larger particle size. |
| 20 | Larger more aggregated particles | anhydrous | Anhydrous at 25% water. Large particle size. |
| 21 | Small irregular chunks with rough surfaces | anhydrous | Reduced $CO_2$ flow. No wt loss on TGA-anhydrous material |

Comparative Example (Runs 27-28)

Water Saturated $CO_2$

As shown in Tables 3 and 4, runs 27 and 28 both utilized a standard T-piece connected prior to the vessel inlet. Water was fed directly into the supercritical $CO_2$ flow at very low flow rates (<0.2 ml.min$^{-1}$) resulting in the water and $CO_2$ being mixed just prior to contact with the organic solution within the SEDS nozzle. The goal was to combine the organic aripiprazole solution with water saturated $CO_2$ at the nozzle. Non-uniform particles with rough surfaces were produced in contrast with the desired well faceted crystalline platelets. The samples, when analyzed by XRPD and DSC, were anhydrous.

Inventive Examples (Runs 22-75)

Water Added to $CO_2$

Further experiments were conducted by introducing water into the supercritical $CO_2$ modifier port. These results are also shown in Tables 3 and 4. Using this methodology water was fed at very low flow rates, into the carbon dioxide at the point within the SEDS process when the $CO_2$ passes through the heat exchanger coils. This allowed the $CO_2$ and the water time to mix fully and homogenize at the elevated temperature, before contacting the organic solution. Excess water not taken up into the $CO_2$ was found to collect in the 50 ml pulse damper vessel prior to the nozzle, minimizing the carry over of water into the product. Attempts to promote the formation of aripiprazole using this experimental set-up (runs 22 and 23) were conducted initially using 1% w/v TBF solutions processed at 200 bar and 60° C., with $CO_2$ flows of 10 ml min$^{-1}$ modified with 0.15 ml.min$^{-1}$ water. Small, irregular, crystalline plates were produced in high yield, i.e., >95%. XRPD analysis of sample 22 confirmed that this material was the monohydrate. The DSC traces of both samples produced from THF showed very distinct, broad de-hydration peaks between 110-120° C., which are indicative of the monohydrate. Small, highly crystalline monohydrate particles could therefore be successfully achieved using this experimental approach. This method was repeated using solutions prepared from n-PrOH to observe if smaller, more uniform crystalline particles of low aspect ratio could be produced whilst maintaining the monohydrate form. In run 29, water was fed via the modifier port, at 0.2 ml.min$^{-1}$ into a $CO_2$ stream of 18 ml.min$^{-1}$ to crystallize aripiprazole from a 6 mg/ml n-PrOH solution at 150 bar and 70° C. The monohydrate was successfully produced, determined by the characteristic DSC trace and XRPD diffractogram. Product yield was high, 87% and pressure fluctuations remained below 20 bar.

The effect of introducing water into the carbon dioxide in this way and allowing time to homogenize clearly had the effect of facilitating hydrate formation from the two solvent/water/$CO_2$ systems investigated. Adequate water was being made available to allow a stable state of hydration to exist within the system while carbon dioxide effectively maintained its anti-solvent property. Several repeat experiments were performed to ensure the repeatability of the process. Runs 44-46, 49-53 and 58-59 all utilized the introduction of low flows of water into the $CO_2$ stream via the modifier port, as shown in Tables 3 and 4. All produced aripiprazole in its monohydrate form. Particle morphology consistently appeared as well faceted, flat, 4-6 sided platelets. Average particle size varied between 4.7-6.3 μm.

A second option for producing water-saturated $CO_2$ for the SEDS production of aripiprazole monohydrate was investigated in runs 61-65. These results are also shown in Tables 3 and 4. A 500 ml stainless steel "saturator" vessel containing up to 100 ml of purified water was connected in-line to the $CO_2$ supply line. This vessel was packed with small stainless steel coils to increase the surface area and so aid equilibration by enhancing the contact area between water and carbon dioxide. The $CO_2$ was pumped through this vessel to incorporate a small proportion of water at its saturation level, less than 1%, before meeting the organic solution within the nozzle. This water-saturated $CO_2$ method was used for runs 61-65. The monohydrate was consistently formed. In run 65, the volume of water required to saturate the $CO_2$ sufficiently was only 30 ml. Processing a saturated n-PrOH solution with a $CO_2$ flow of 20 ml.min$^{-1}$ at 150 bar and 50° C. resulted in the formation of thin, slightly irregular, crystalline platelets when observed by SEM. It was clear that the size of the particles produced in this way had increased slightly and also demonstrated a wider size distribution. The lowest sample VMD was 6.5 μm compared with particles of 4.7 μm produced using the modifier port approach.

It was established, however, that this method successfully resulted in the formation of the monohydrate polymorph. The DSC trace of run 65 clearly exhibited a large dehydration peak around 120° C. As a result of processing using fully water-saturated $CO_2$, it was not possible to dry the crystallized material during the $CO_2$ only drying stage, and the end of the experiment. This resulted in the recovery of a slightly damp product. This material was shown by DSC to remain hydrated, after slow drying in a desiccator.

The inventive examples of runs 66-75 included the method of using a saturator vessel to introduce water to the supercritical fluid. The 500 ml saturator vessel was again connected in-line to the process. The water volume within the saturator was varied between 50-150 ml and the $CO_2$ flow rates were increased by a factor of 5-10 times from those employed in the lab-scale process. SEDS™ processing of saturated n-PrOH solutions, using the standard 2-component nozzle configuration/water saturator, was carried out at 150 bar and 70° C. The $CO_2$ flow rate and water volume, two parameters that greatly influence the residence time of $CO_2$ within the water rich saturator environment, were shown to affect the state of aripiprazole hydration.

Run 67, utilizing a very high $CO_2$ flow of 200 ml.min$^{-1}$ in combination with a low water volume of 50 ml, resulted in the formation of small, highly crystalline platelets. The material was anhydrous by DSC, as only a single melt peak was observed. The particle size and morphology of this sample were equivalent to those of samples produced using the modifier port. Repeating the experiment but reducing the $CO_2$ flow to 150 ml.min$^{-1}$ and increasing the volume of water in the saturator to 100 ml, increased the water/$CO_2$ contact time. Run 69 resulted in the formation of hydrated aripiprazole. This was confirmed by the characteristic XRPD diffractogram. As a result of reduced supersaturation effected by the lower flow rate and increased water content of the supernatural $CO_2$ mixture, particle size was shown to have increased to 8.1 μm VMD. Particle morphology, observed by SEM, was more irregular than the anhydrous sample, consisting of larger crystalline bars and plates up to 25 μm in size.

A sonic nozzle method was used in runs 70-75. The major difference between this method and the standard 2-component nozzle is that the solution stream is applied separately through a narrow bore solution line. The solution and supercritical $CO_2$ streams then meet outside the nozzle aperture. This approach was employed to observe the effect of sonic velocity processing conditions on a particle size and morphology. The 500 ml saturator was incorporated into the process, including 100-150 ml of purified water. Saturated n-PrOH solutions were processed using extremely high velocity $CO_2$ (>200 ml.min$^{-1}$) with solution flows of 1-4 ml.min$^{-1}$. Pressure/temperature combinations of 100 bar, 50° C. and 80 bar, 35° C. were employed as these conditions produced $CO_2$ densities suited to "sonic" processing. Although highly crystalline monohydrate particles were formed readily using this experimental approach, the samples displayed a flat, platelet habit of irregular size and morphology. The sample also demonstrated that the lowest monohydrate particle size, which could be achieved using this technique, was 7.8 μm. It was clear from the SEM images that the particles were irregular and covered a wide size distribution.

Both methods of adding the water through the modifier port and the use of the saturator vessel (with the sonic nozzle as well as the two component nozzle) successfully and consistently produced the desired monohydrate form.

TABLE 3

WATER SATURATED $CO_2$

| Run | Solvent (v/v) | Soln conc. (w/v) | Soln flow (ml/min) | CO Flow (ml/min) | Pressure (bar) | Temp (° C.) | AP (bar) | Nozzle (mm) | Yield (%) | VMD (μm) |
|---|---|---|---|---|---|---|---|---|---|---|
| 22 | THF | 1.0 | 0.2 | 10 + 0.15 $H_2O$ | 200 | 60 | 20 | 0.2 | 99 | — |
| 23 | THF | 1.0 | 0.2 | 10 + 0.15 $H_2O$ | 200 | 60 | 30 | 0.2 | 98 | — |
| 24 | n-PrOH | 0.6 | 0.3 | 18 | 150 | 70 | 30 | 0.2 | 98 | 6.2 |
| 25 | n-PrOH | 0.6 | 0.6 | 18 | 150 | 70 | 25 | 0.2 | 97 | 51 |
| 26 | n-PrOH | 0.6 | 1.0 | 18 | 150 | 70 | 10 | 0.2 | 90 | — |
| 27 | n-PrOH | 0.6 | 0.5 | 18 + 0.2 $H_2O$ | 150 | 70 | 10 | 0.2 | 75 | — |
| 28 | n-PrOH | 0.6 | 0.5 | 18 + 0.05 $H_2O$ | 150 | 70 | 25 | 0.2 | 88 | — |
| 29 | n-PrOH | 0.6 | 0.3 | 18 + 0.2 $H_2O$ | 150 | 70 | 20 | 0.2 | 87 | — |
| 30 | n-PrOH | 0.6 | 0.3 | 18 | 150 | 70 | 15 | 0.2 | 99 | — |
| 31 | n-PrOH | 0.6 | 0.4 | 18 + 0.2 $H_2O$ | 150 | 70 | 10 | 0.2 | — | — |
| 32 | n-PrOH | 0.6 | 0.5 | 9 | 150 | 50 | 35 | 0.2 | 68 | 20.3 |
| 33 | n-PrOH | 0.6 | 0.75 | 9 | 150 | 50 | 5 | 0.2 | 75 | 18.5 |
| 34 | n-PrOH | 0.6 | 1.0 | 20 | 150 | 70 | 30 | 0.2 | 80 | 13.6 |
| 35 | n-PrOH | 0.6 | 1.0 | 20 | 150 | 70 | 20 | 0.2 | 84 | 12.3 |
| 36 | n-PrOH | 0.6 | 0.3 | 20 | 150 | 70 | 30 | 0.2 | 80 | 4.7 |
| 37 | n-PrOH | 0.6 | 3.0 | 200 | 150 | 65 | 10 | 0.4 | 81 | 7.7 |
| 38 | n-PrOH | 0.6 | 0.3 | 20 | 150 | 70 | 20 | 0.2 | 77 | 5.9 |
| 39 | n-PrOH | 0.6 | 0.3 | 20 | 150 | 70 | 30 | 0.2 | 80 | 10.0 |
| 40 | n-PrOH | 0.6 | 0.3 | 20 | 150 | 70 | 40 | 0.2 | 90 | 7.7 |
| 41 | n-PrOH | 0.65 | 0.3 | 18 | 150 | 70 | 20 | 0.2 | 95 | 11.5 |
| 42 | n-PrOH | 0.6 | 0.2 | 18 | 150 | 70 | 65 | 0.2 | 90 | 6.7 |
| 43 | n-PrOH | 0.6 | 0.3 | 18 | 150 | 70 | 65 | 0.2 | 25 | 5.8 |
| 44 | n-PrOH | 0.6 | 0.3 | 18 + 0.15 $H_2O$ | 150 | 70 | 10 | 0.2 | ~100 | 4.7 |
| 45 | n-PrOH | 0.6 | 0.3 | 18 + 0.15 $H_2O$ | 150 | 70 | 20 | 0.2 | 90 | 5.1 |
| 46 | n-PrOH | 0.6 | 1.0 | 18 + 0.15 $H_2O$ | 150 | 70 | 40 | 0.2 | 84 | 8.4 |
| 47 | n-PrOH | 0.6 | 0.5 | 20 | 150 | 70 | 20 | 0.2 | 89 | 4.7 |
| 48 | n-PrOH | 0.6 | 0.5 | 20 + 0.15 $H_2O$ | 150 | 70 | 25 | 0.2 | 92 | 5.7 |
| 49 | n-PrOH | 0.6 | 0.5 | 16 + 0.1 $H_2O$ | 150 | 70 | 25 | 0.2 | 99 | 6.2 |
| 50 | n-PrOH | 0.6 | 0.3 | 18 + 0.15 $H_2O$ | 150 | 70 | 25 | 0.2 | 96 | 6.2 |
| 51 | n-PrOH | 0.6 | 0.3 | 18 + 0.15 $H_2O$ | 150 | 70 | 20 | 0.2 | ~100 | 5.8 |
| 52 | n-PrOH | 0.6 | 0.3 | 18 + 0.15 $H_2O$ | 150 | 70 | 20 | 0.2 | ~100 | — |
| 53 | n-PrOH | 0.6 | 0.5 | 20 + 0.15 $H_2O$ | 150 | 70 | 30 | 0.2 | 89 | — |
| 54 | n-PrOH | 0.6 | 0.3 | 20 | 150 | 70 | 25 | 0.2 | — | — |
| 55 | n-PrOH | 0.6 | 0.3 | 20 | 150 | 70 | 20 | 0.2 | 92 | — |
| 56 | n-PrOH | 0.6 | 0.3 | 18 + 0.15 $H_2O$ | 150 | 70 | 12 | 0.2 | 89 | — |
| 57 | n-PrOH | 0.6 | 1.0 | 100 + 0.75 $H_2O$ | 150 | 67 | 6 | 0.4 | — | — |
| 58 | n-PrOH | 0.6 | 0.3 | 18 + 0.15 $H_2O$ | 150 | 70 | 25 | 0.2 | 89 | — |

TABLE 3-continued

WATER SATURATED CO$_2$

| Run | Solvent (v/v) | Soln conc. (w/v) | Soln flow (ml/min) | CO Flow (ml/min) | Pressure (bar) | Temp (°C.) | AP (bar) | Nozzle (mm) | Yield (%) | VMD (μm) |
|---|---|---|---|---|---|---|---|---|---|---|
| 59 | n-PrOH | 0.6 | 0.3 | 18 + 0.15 H$_2$O | 150 | 70 | 25 | 0.2 | 68 | — |
| 60 | n-PrOH | 0.6 | 0.3 | 18 | 150 | 40 | 30 | 0.2 | 72 | — |
| 61 | n-PrOH | 0.6 | 0.3 | 20 | 150 | 70 | 15 | 0.2 | ~100 | — |
| 62 | n-PrOH | 0.6 | 0.3 | 20 | 150 | 70 | 25 | 0.2 | ~100 | — |
| 63 | n-PrOH | 0.6 | 0.3 | 20 | 150 | 70 | 20 | 0.2 | ~100 | 6.9 |
| 64 | n-PrOH | 0.6 | 0.3 | 20 | 150 | 70 | 15 | 0.2 | ~100 | 7.3 |
| 65 | n-PrOH | 0.6 | 0.3 | 20 | 150 | 50 | 15 | 0.2 | ~100 | 6.5 |
| 66 | n-PrOH | 0.6 | 2.0 | 100 | 150 | 68 | 20 | 0.4 | 83 | — |
| 67 | n-PrOH | 0.6 | 2.0 | 200 | 150 | 65 | 35 | 0.4 | 90 | 6.4 |
| 68 | n-PrOH | 0.6 | 2.0 | 100 | 150 | 63 | 70 | 0.2 | 77 | 9.1 |
| 69 | n-PrOH | 0.6 | 2.0 | 150 | 150 | 62 | 100 | 0.2 | 75 | 8.1 |
| 70 | n-PrOH:H$_2$O (33:1) | 0.58 | 2.0 | 200 | 150 | 62 | OP | Sonic 0.2 | 79 | 8.3 |
| 71 | n-PrOH | 0.6 | 2.0 | 180 | 80 | 37 | 0 | Sonic 0.2 | — | — |
| 72 | n-PrOH | 0.6 | 4.0 | >200 | 80 | 37 | 0 | Sonic 0.2 | 78 | 11.0 |
| 73 | n-PrOH | 0.6 | 1.0 | >200 | 100 | 48 | 0 | Sonic 0.2 | 81 | 7.8 |
| 74 | n-PrOH | 0.6 | 4.0 | >200 | 80 | 38 | 0 | Sonic 0.2 | 83 | 13.2 |
| 75 | acetone | 3.0 | 4.0 | >200 | 100 | 50 | 0 | Sonic 0.2 | — | — |

TABLE 4

WATER-SATURATED CO$_2$

| Run | Morphology (SEM) | DSC/XRPD | Notes |
|---|---|---|---|
| 22 | Well faceted crystalline particles | Monohydrate/Monohydrate | Sample was slightly wet, water introduced via CO$_2$ modifier port |
| 23 | Well faceted crystalline particles | Monohydrate/Monohydrate | Repeat of 22 |
| 24 | Small well defined prismatic slabs/plates, <6 μm | Monohydrate/Monohydrate | Water contamination in pulse damper from previous runs (CO$_2$ stream wet) |
| 25 | Small well defined slabs/plates, <6 μm | anhydrous/N1 | No water contamination |
| 26 | Small well defined slabs/plates, <6 μm | anhydrous | Particle size stays small after large increase in solution flow rate |
| 27 | Non-uniform particles with rough surfaces | anhydrous/N1 | Water via T-piece. Powder more dense, different morphology |
| 28 | Non-uniform particles with rough surfaces | anhydrous | Water via T-piece. Powder more dense, different morphology |
| 29 | Thin slabs/plates <20 μm | Monohydrate/Monohydrate | Water via CO$_2$ modifier port. TGA = 3% wt loss due to water |
| 30 | Thin prismatic slabs/plates, all <20 μm | Monohydrate/Monohydrate | CO$_2$ passed through a wet pulse damper (PD) to pick up water |
| 31 | — | Monohydrate | Water via CO$_2$ modifier port. No pulse damper. Damp product. |
| 32 | Large irregular chunks up to 150 μm | anhydrous/N1 | CO$_2$ flow reduced to produce larger anhydrous particles |
| 33 | Large irregular chunks up to 150 μm | — | Solution flow increase further. Little size difference. |
| 34 | Plates 5-30 μm | — | Repeat of 26 with a larger 500 ml vessel |
| 35 | — | anhydrous | Kit modification. 15 ml H$_2$o in 1$^{st}$ PD. Bypass to dry PD with EtOH mod. 500 ml |
| 36 | Small uniform plates <6 μm | anhydrous | Kit modification. 10 ml H$_2$O in 1$^{st}$ PD. Bypass to dry PD without EtOH mod. 500 ml. |
| 37 | Small uniform plates | anhydrous | Pilot Plant batch (4.3 g). Scale up of trial 37 to produce an anhydrous batch. |
| 38 | Small crystalline slabs/plates 2-8 μm in size | anhydrous | Kit modification. 15 ml H$_2$O in 1$^{st}$ PD. Vessel filled, run and dried via 1$^{st}$ PD only. |
| 39 | Irregular crystalline chunks with rough surfaces | anhydrous | Kit modification. 15 ml H$_2$O in 1$^{st}$ PD. Bypass to dry PD for drying stage. |
| 40 | Irregular crystalline plates up to 30 μm in size | Monohydrate | Repeat of 30 using original set-up. Wet 1$^{st}$ pulse damper |

TABLE 4-continued

WATER-SATURATED $CO_2$

| Run | Morphology (SEM) | DSC/XRPD | Notes |
|---|---|---|---|
| 41 | Irregular flat crystalline plates. Some very large | Monohydrate | Kit modification. 15 ml $H_2O$ in $2^{nd}$ PD. Vessel filled, run dried via $2^{nd}$ PD only |
| 42 | Small well defined prismatic slabs/plates, <6 μm | anhydrous/N1 | Repeat of 24 to produce the monohydrate (anhydrate formed) |
| 43 | Small well defined prismatic slabs/plates, <6 μm | anhydrous/N1 | Repeat of 24 and 42 using a different Kit (anhydrate formed) |
| 44 | Small well defined prismatic slabs/plates, <6 μm | Monohydrate/Monohydrate | Water via $CO_2$ modifier port. Pulse damper full of water at end of run. Damp product. |
| 45 | Small well defined prismatic slabs/plates <6 μm | Monohydrate/Monohydrate | Repeat of 44. Sample was slightly wet, water introduced via $CO_2$ modifier port. |
| 46 | Irregular prismatic slabs/plates, mostly <10 μm | Monohydrate/Monohydrate | Water introduced via $CO_2$ modifier port. Increased throughput gives larger particles. |
| 47 | Uniform, well faceted crystalline particles <6 μm | anhydrous/N1 | Anhydrous conditions employed but material dried with wet $CO_2$ |
| 48 | Well faceted prismatic crystals <10 μm in size | anhydrous | Water introduced via $CO_2$ modifier port, but stopped mid way through run-anhydrous? |
| 49 | Well faceted 4-6 sided crystals mostly <10 μm | Monohydrate | Water introduced via $CO_2$ modifier port for entire run. |
| 50 | Well faceted 4-6 sided crystals mostly <10 μm | Monohydrate | Repeat of runs 44 and 45 to produce a 2 g batch for BMS |
| 51 | Well faceted 4-6 sided crystals mostly <10 μm | Monohydrate | Repeat to produce a 2 g batch for BMS |
| 52 | Well faceted 4-6 sided crystals mostly <10 μm | Monohydrate | Repeat to produce a 2 g batch for BMS |
| 53 | — | Monohydrate | Water introduced via $CO_2$ modifier port. 500 ml vessel. Monohydrate still produced. |
| 54 | — | anhydrous | Produce anhydrous material and then pass wet $CO_2$ over product. Run abandoned due to leak. |
| 55 | — | anhydrous | Anhydrous conditions employed but dried using wet $CO_2$ via a $2^{nd}$ PD with water. |
| 56 | — | anhydrous | Repeat monohydrate production (52) on a different Kit. Appears not reproducible. |
| 57 | — | — | Pilot Plant. Water introduced directly into $CO_2$ stream. Slushy, wet product on filter. |
| 58 | — | Monohydrate/Monohydrate | Water introduced via $CO_2$ modifier port for entire run. Repeat 56. |
| 59 | — | Monohydrate/Monohydrate | Water introduced via $CO_2$ modifier port for entire run. Repeat 58 but short run. |
| 60 | — | Monohydrate | 20 ml $H_2O$ in PD used as a $CO_2$ saturator vessel. Reduced temperature also. |
| 61 | Irregular flat crystalline particles up to 20 μm in size | Monohydrate/Monohydrate | 100 ml $H_2O$ in 500 ml saturator. Damp material (yield >100%). |
| 62 | — | anhydrous | 50 ml $H_2O$ in 500 ml saturator. Damp material. Reduced water content = anhydrous product. |
| 63 | Irregular crystalline plates up to 30 μm in size | Monohydrate/Monohydrate | 100 ml $H_2O$ in 500 ml saturator. Damp material (yield >100%). Repeat of 61. |
| 64 | Irregular crystalline plates up to 30 μm in size | Monohydrate/Monohydrate | 100 ml $H_2O$ in 500 ml saturator. 50 ml vessel after saturator for XS water. Damp material. |
| 65 | Irregular crystalline plates up to 30 μm in size | Monohydrate/Monohydrate | 30 ml $H_2O$ in 500 ml saturator. Slightly reduced temperature. Damp material. |
| 66 | Very large, irregular, crystalline plates up to 250 μm. | Monohydrate/Monohydrate | Pilot Plant-Saturator. 100 ml $H_2O$ in 500 ml saturator. Damp material |
| 67 | — | anhydrous | Pilot Plant-Saturator. 50 ml $H_2O$ 500 ml saturator. Increased $CO_2$ flow and raised filter. |
| 68 | Irregular crystalline plates up to 20 μm in size | Monohydrate/Monohydrate | Pilot Plant-Saturator. 100 ml $H_2O$ in 500 ml saturator. Damp material. |
| 69 | Irregular crystalline plates up to 20 μm in size | Monohydrate/Monohydrate | Pilot Plant-Saturator. 100 ml $H_2O$ in 500 ml saturator. Increased $CO_2$ flow. Damp. |
| 70 | Irregular crystalline plates up to 30 μm in size | Monohydrate | Sonic Nozzle-Saturator. 150 ml $H_2O$ in 500 ml saturator. Solution crashing out (OP) |
| 71 | — | — | Sonic Nozzle-Saturator. 150 ml $H_2O$ in 500 ml saturator. Wet slushy product |
| 72 | — | Monohydrate/Monohydrate | Sonic Nozzle-Saturator. 100 ml $H_2O$ in 500 ml saturator. Raised filter. Damp powder |
| 73 | — | Monohydrate | Sonic Nozzle-Saturator. 100 ml $H_2O$ in 500 ml saturator. Raised filter. Damp powder |
| 74 | — | Monohydrate | Sonic Nozzle-Saturator. 100 ml $H_2O$ in 500 ml saturator. Raised filter. Damp powder |

TABLE 4-continued

WATER-SATURATED $CO_2$

| Run | Morphology (SEM) | DSC/XRPD | Notes |
|---|---|---|---|
| 75 | — | — | Sonic Nozzle-Saturator. 100 ml $H_2O$ in 500 ml saturator. Wet slushy product. |

SEM = Scanning electron microscop

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. A process for preparing a crystalline aripiprazole monohydrate from unprocessed aripiprazole comprising the steps of:
    (a) providing a first mixture comprising a solvent and unprocessed aripiprazole;
    (b) providing a second mixture comprising a supercritical fluid which is carbon dioxide, nitrous oxide, sulfur hexafluoride, xenon, ethylene, chlorotrifluoromethane, ethane, trifluoromethane, or combinations thereof and optionally a modifier, which modifier is either completely miscible with, or is at least partially soluble in both the supercritical fluid and water, and which modifier is methanol, ethanol, n-propanol (n-PrOH), isopropanol, n-butanol, iso-butanol, sec-butanol, tert-butanol, an aldehyde, acetone, dimethylsulfoxide, tetrahydrofuran (THF), dichloromethane, dimethyl formamide (DMF), or combinations thereof;
    (c) introducing water to the second mixture;
    (d) introducing the first mixture and the second mixture into a particle formation vessel, wherein the contacting of the first mixture with the second mixture produces crystalline aripiprazole monohydrate; and
    (e) recovering the crystalline aripiprazole monohydrate.

2. The process of claim 1, further comprising the step of allowing the water and the second mixture to homogenize prior to contact with the first mixture.

3. The process of claim 1, wherein introducing water to the second mixture is conducted by a process selected from the group consisting of:
    (a) pumping the water into a supply line through which the second mixture flows; and
    (b) pumping the second mixture through a saturator vessel comprising the water.

4. The process of claim 3, wherein said saturator vessel further comprises stainless steel coils.

5. The process of claim 1, wherein the first mixture further comprises water.

6. The process of claim 1, wherein the solvent comprises a substance selected from the group consisting of methanol, ethanol, n-propanol, isopropanol, n-butanol, iso-butanol, sec-butanol, ethyl acetate, acetonitrile, tert-butanol, an aldehyde, acetone, dimethylsulfoxide, tetrahydrofuran, dichloromethane, dimethyl formamide, and combinations thereof.

7. The process of claim 1, wherein the solvent comprises n-propanol.

8. The process of claim 1, wherein the supercritical fluid comprises carbon dioxide.

9. The process of claim 1, further comprising the steps of discontinuing the introducing of the first mixture, discontinuing the introducing of water to the second mixture, and introducing additional amounts of the second mixture to the particle formation vessel before recovering the crystalline aripiprazole.

10. The process of claim 1, wherein the modifier comprises up to about 20% of said second mixture.

11. The process of claim 1, wherein the modifier comprises from about 1% to about 20% of the second mixture.

12. The process of claim 1, wherein the second mixture has a flow rate of about 9 mL/min or greater.

13. The process of claim 1, wherein the first mixture has a flow rate of about 0.4 mL/min or less.

14. The process of claim 3, wherein the water has a flow rate of about 0.2 mL/min or less.

15. The process of claim 1, wherein the crystalline aripiprazole comprises particles of a size range from about 1 μm to about 75 μm.

16. The process of claim 1, wherein the crystalline aripiprazole comprises particles of a size range preferably from about 2 μm to about 25 μm.

17. The process of claim 1, wherein the simultaneous introduction of the first mixture and the second mixture is effected through a coaxial nozzle.

18. A process for preparing a crystalline aripiprazole monohydrate from unprocessed aripiprazole comprising the steps of:
    (a) providing a first mixture comprising n-propanol and unprocessed aripiprazole;
    (b) providing a second mixture comprising supercritical carbon dioxide and optionally a modifier, which modifier is either completely miscible with, or is at least partially soluble in both the supercritical fluid and water, and which modifier is methanol, ethanol, n-propanol,(n-PrOH), isopropanol, n-butanol, iso-butanol, sec-butanol, tert-butanol, an aldehyde, acetone, dimethylsulfoxide, tetrahydrofuran (THF), dichloromethane, dimethyl formamide (DMF), or combinations thereof;
    (c) introducing water to the second mixture at a flow rate of about 0.2 L/min or less;
    (d) introducing the first mixture, at a flow rate of about 0.4 mL/min or less, and the second mixture, at a flow rate of about 9 mL/min or greater, into a particle formation vessel wherein the contacting of the first mixture with the second mixture produces crystalline aripiprazole monohydrate; and
    (e) recovering the crystalline aripiprazole monohydrate.

* * * * *

UNITED STATES PATENT AND TRADEMARK OFFICE
CERTIFICATE OF CORRECTION

PATENT NO. : 7,507,823 B2
APPLICATION NO. : 11/124216
DATED : March 24, 2009
INVENTOR(S) : David Worthen et al.

It is certified that error appears in the above-identified patent and that said Letters Patent is hereby corrected as shown below:

On the Title Page, Item (54) and in the specification, Column 1, lines 1 to 2, change "PROCESS OF MAKING ARIPIPRAZOLE PARTICLES" to -- PROCESS FOR MAKING ARIPIPRAZOLE PARTICLES --.

Title Page, Item (56) References Cited: Column 2 (Other Publications), line 1, delete "Porperties" and insert -- Properties --.

In the Specification:

Column 1, line 3, insert -- CROSS REFERENCE TO RELATED APPLICATIONS --.

In the Claims:

Claim 18:

Column 20, line 44, delete "n-propanol," and insert -- n-propanol --.

Column 20, line 50, delete "0.2L/min" and insert -- 0.2mL/min --.

Signed and Sealed this
Thirteenth Day of August, 2013

Teresa Stanek Rea
*Acting Director of the United States Patent and Trademark Office*